US006362321B1

(12) United States Patent
Seiden et al.

(10) Patent No.: US 6,362,321 B1
(45) Date of Patent: Mar. 26, 2002

(54) TAXOL RESISTANCE ASSOCIATED GENE

(75) Inventors: Michael V. Seiden, Wayland; Zhenfeng Duan, Cambridge; Aynn Feller, Somerville, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/277,303

(22) Filed: Mar. 26, 1999

Related U.S. Application Data (60) Provisional application No. 60/079,771, filed on Mar. 27, 1998.

(51) Int. Cl.[7] .................. C07H 19/00; C07H 21/00; C07H 5/04; C07H 5/06; C07H 21/04
(52) U.S. Cl. .................. 536/22.1; 536/18.7; 536/23.1; 536/23.5; 435/320.1; 435/325; 435/455
(58) Field of Search .................. 536/18.7, 22.1, 536/23.1, 23.5; 435/455, 325, 320.1

(56) References Cited

U.S. PATENT DOCUMENTS 5,705,343 A  * 1/1998 Drayna et al.

OTHER PUBLICATIONS

Bork, Peer. Powers and Pitfalls in Sequence Analysis: The 70% Hurdle. Genome Research 10:398–400, 2000.*
Nucleic acid database, Accession #H03444, 1995.*
Duan et al. TRAG–3, a novel gene, isolated from a taxol-–resistant ovarian carcinoma cell line. Gene 229(1–2):75–81, Mar. 18, 1999.*
Casazza et al., "Paclitaxel (Taxol) Mechanism of Resistance (Chapter 6)," in Drug Resistance, William N. Halt, M.D., Ph.D., editor, ©(1996).
Giannakakou et al., "Paclitaxel–resistant Human Ovarian Cancer Cells Have Mutant β–Tubulins That Exhibit Impaired Paclitaxel–driven Polymerization," The Journal of Biological Chemistry 272:17118–17125, 1997.
Gottesman et al., "The Biochemistry of Multidrug Resistance Mediated by the Multidrug Transporter" Annu. Rev. Biochem. 1993. 62:385–427.
Haber et al., "Altered Expression of Mβ2, the Class II β–Tubulin Isotype, in a Murine J774.2 Cell Line with a High Level of Taxol Resistance," The Journal of Biological Chemistry 270: 31269–31275, 1995.
Horwitz et al., "Taxol: Mechanisms of Action and Resistance," Journal of the National Cancer Institute Monographs No. 15: 55–61 (1993).
Johnson et al., "Paclitaxel Plus Carboplatin in Advanced Non–Small–Cell Lung Cancer: A Phase II Trial," Journal of Clinical Oncology, 14:2054–2060, 1996.
McGuire et al., "Cyclophosphamide and Cisplatin Compared with Paclitaxel and Cisplatin in Patients with Stage III and Stage IV Ovarian Cancer," The New England Journal of Medicine, 334:1–6, 1996.
Van Der Zee et al., "Cell Biological Markers of Drug Resistance in Ovarian Carcinoma," Gynecologic Oncology 58:165–178 (1995).
Wahl et al., "Loss of Normal p53 function confers sensitization to Taxol by increasing G2/M arrest and apoptosis," Nature Medicine, 2:72–79, 1996.

* cited by examiner

*Primary Examiner*—Anthony C. Caputa
*Assistant Examiner*—Alana M. Harris
(74) *Attorney, Agent, or Firm*—Fish & Richardson, P.C.

(57) ABSTRACT

A gene overexpressed in taxol-resistant cancer cell lines is disclosed. The gene is designated Taxol Resistance Associated Gene-3 ("TRAG-3"). At least two alternatively spliced forms of TRAG-3 exist. TRAG-3 polypeptides, TRAG-3 antibodies, and TRAG-3-related screening methods useful in drug discovery are also disclosed.

15 Claims, 4 Drawing Sheets

FIG. 1

```
  1 GTGCAATGGCTAGTACTATGTGTCAACTTGTCTAGGCTATACTGCTCAGCTGTGTGGTCA    60

61 AACAGTAGTCTAGATGTTGCTGTGAAGGTATTTTGTAGATGTGATCAACATTTA CAATCA  120

121 GTTGATTTTAAGTAAAGCAGTTTAACTTCCAATATGTGGATGGGCCTCATCCAATTAGTT  180
  1                                       M  W  M  G  L  I  Q  L  V    9

181 GAAGGTGTTAAGAGAAAAGACCAAGGTTTCCTGGAAAAGGAATTCTACCACAAGACTAAC  240
 10  E  G  V  K  R  K  D  Q  G  F  L  E  K  E  F  Y  H  K  T  N    29

241 ATAAAAATGCACTGTGAGTTTCTAGCCTGCTGGCCTGCCTTCACTGTCCTGGGGAGGCT   300
 30  I  K  M  H  C  E  F  L  A  C  W  P  A  F  T  V  L  G  E  A    49

301 TGGAGAGACCAGGTGGACTGGAGTATACTGTTGAGAGACGCTGGTCTGGTGAAGATGTCC  360
 50  W  R  D  Q  V  D  W  S  I  L  L  R  D  A  G  L  V  K  M  S    69

361 AGGAAACCACGAGCCTCCAGCCCATTGTCCAACAACCACCCACCAACACCAAAGAGGTTC  420
 70  R  K  P  R  A  S  S  P  L  S  N  N  H  P  P  T  P  K  R  F    89

421 CCAAGACAACTCGGAAGGGAAAAGGGACCCATCGAGGAAGTTCCAGGAACAAAAGGCTCT  480
 90  P  R  Q  L  G  R  E  K  G  P  I  E  E  V  P  G  T  K  G  S   109

481 CCATAAAAGACCGCCGCTTCAAAAAAACCTGAGGAATGGAGTGGGCCAACACTATCCAGC  540
110  P  *  (SEQ ID NO: 2)

541 CACTCTGACCAGCCGAACGAGGAACTCAATCAAAATGAGCCATAGCGGGACCACAAGGGC  600

601 AAGGAGACCACCACTTTCTCCAGTCTCTTTTCGGACAGCCAGTAATTCCCGGGCAAGGCC  660

661 AGAGACTTCAAGTCTATCTGAAAAGTCTCCAGAGGTCTAACCCCAGATAAATAGCCAACA  720

721 GGGTGTAGAGTACGTTTTACACCCCAAAGGGTATGCCCCATGTGATGGAAATAAAATGAA  780

781 CATGTTGTAAAAAAAAAAA    (SEQ ID NO: 1)
```

FIG. 2

```
GTGCAATTGCTAGTACTATGTGTCAACTTGTCTAGGCTATACTGCTCAGCTGTGTGGTCAAACAG
TAGTCTAGATGTTGCTGTGAAGGTATTTTGTAGATGTGATCAACATTTACAATCAGTTGATTTTA
AGTAAAGCAGTTTAACTTCCAATATGTGGATGGGCCTCATCCAATTAGTTGAAGGTGTTAAGAGA
AAAGACCAAGGTTTCCTGGAAAAGGAATTCTACCACAAGACTAACATAAAAATGCACTGTGAGTT
TCATGCCTGCTGGCCTGCCTTCACTGTCCTGGGGGAGGCTTGGAGAGACCAGGTGGACTGGAGTA
TACTGTTGAGAGACGCTGGTCTGGTGAAGATGTCCAGGAAACCACGAGCCTCCAGCCCATTGTCC
AACAACCACCCACCAACACCAAAGAGgcgaggaagtggaaggcatcctctcaaccctggcccaga
agccctatcaaaGTTCCCAAGACAACTCGGAAGGGAAAAGGGACCCATCGAGGAAGTTCCAGGAA
CAAAAGGCTCTCCATAAAAGACCGCCGCTTCAAAAAAACCTGAGGAATGGAGTGGGCCAACACTA
TCCAGCCACTCTGACCAGCCGAACGAGGAACTCAATCAAAATGAGCCATAGCGGGACCACAAGGG
CAAGGAGACCACCACTTTCTCCAGTCTCTTTTCGGACAGCCAGTAATTCCCGGGCAAGGCCAGAG
ACTTCAAGTCTATCTGAAAAGTCTCCAGAGGTCTAACCCCAGATAAATAGCCAACAGGGTGTAGA
GTACGTTTTACACCCCAAAGGGTATGCCCCATGTGAGGGAAATAAAATGAACATGTTGTAAAAAA
AAAAA
```

FIG. 3

| M | W | M | G | L | I | Q | L | V | E | G | V | K | R | K | D | Q |
|---|---|---|---|---|---|---|---|---|---|---|---|---|---|---|---|---|
| G | F | L | E | K | E | F | Y | H | K | T | N | I | K | M | H | C |
| E | F | H | A | C | W | P | A | F | T | V | L | G | E | A | W | R |
| D | Q | V | D | W | S | I | L | L | R | D | A | G | L | V | K | M |
| S | R | K | P | R | A | S | S | P | L | S | N | N | H | P | P | T |
| P | K | R | R | G | S | G | R | H | P | L | N | P | G | P | E | A |
| L | S | K | F | P | R | Q | L | G | R | E | K | G | P | I | E | E |
| V | P | G | T | K | G | S | P | * |   |   |   |   |   |   |   |   |

FIG. 4

| Cell Line | Tumor Type | TRAG-3 | MDR-1 |
|---|---|---|---|
| CCRF-CEM | Leukemia | - | - |
| HL-60(TB) | Leukemia | + | - |
| K-562 | Leukemia | + | - |
| MOLT-4 | Leukemia | - | - |
| RPMI-8226 | Leukemia | + | - |
| SR | Leukemia | + | - |
| A549/ATCC | NSCLC | - | - |
| EKVX | NSCLC | + | -/+ |
| HOP-62 | NSCLC | + | + |
| HOP-92 | NSCLC | + | - |
| NCI-H226 | NSCLC | - | + |
| NCI-H23 | NSCLC | + | - |
| NCI-H322M | NSCLC | + | - |
| NCI-H460 | NSCLC | + | - |
| NCI-H522 | NSCLC | - | - |
| COLO 205 | Colon | - | - |
| HCC-2998 | Colon | - | - |
| HCT-116 | Colon | + | -/+ |
| HCT-15 | Colon | + | + |
| SW-620 | Colon | - | + |
| SF-268 | CNS | + | - |
| SF-295 | CNS | + | + |
| SF-539 | CNS | + | - |
| SNB-19 | CNS | + | - |
| SNB-75 | CNS | + | - |
| U251 | CNS | + | - |
| LOX IMVI | Melanoma | + | + |
| MALME-3M | Melanoma | - | + |
| M14 | Melanoma | + | + |
| SK-MEL-2 | Melanoma | + | + |
| SK-MEL-28 | Melanoma | + | + |
| UACC-257 | Melanoma | + | + |
| UACC-62 | Melanoma | + | -/+ |
| IGROV1 | Ovarian | - | - |
| OVCAR-3 | Ovarian | - | - |
| OVCAR-4 | Ovarian | + | - |
| OVCAR-5 | Ovarian | - | - |
| OVCAR-8 | Ovarian | - | -/+ |
| SK-OV-3 | Ovarian | + | - |
| 786-0 | Renal | + | - |
| A498 | Renal | - | + |
| ACHN | Renal | + | + |
| CAKI-1 | Renal | - | + |
| RXF-393 | Renal | - | + |
| SN12C | Renal | + | - |
| TK-10 | Renal | - | - |
| UO-31 | Renal | + | + |
| PC-3 | Prostate | + | ND |
| MCF-7 | Breast | - | ND |
| MCF7/ADR-RES | Breast | - | ND |
| MDA-MB-231/ATCC | Breast | - | ND |
| HS 587T | Breast | + | ND |
| MDA-MB-435 | Breast | + | ND |
| MDA-N | Breast | + | ND |
| BT-549 | Breast | + | ND |
| T-47D | Breast | - | ND |

FIG. 5

SEQUENCE LISTING

```
<160> NUMBER OF SEQ ID NOS: 4

<210> SEQ ID NO 1
<211> LENGTH: 799
<212> TYPE: DNA
<213> ORGANISM: Homo sapiens
<220> FEATURE:
<221> NAME/KEY: CDS
<222> LOCATION: (154)..(483)

<400> SEQUENCE: 1
gtgcaatggc tagtactatg tgtcaacttg tctaggctat actgctcagc tgtgtggtca      60
```

-continued

```
aacagtagtc tagatgttgc tgtgaaggta ttttgtagat gtgatcaaca tttacaatca    120
gttgatttta agtaaagcag tttaacttcc aat atg tgg atg ggc ctc atc caa    174
                                    Met Trp Met Gly Leu Ile Gln
                                      1               5 tta gtt gaa ggt gtt aag aga aaa gac caa ggt ttc ctg gaa aag gaa    222
Leu Val Glu Gly Val Lys Arg Lys Asp Gln Gly Phe Leu Glu Lys Glu
         10                  15                  20 ttc tac cac aag act aac ata aaa atg cac tgt gag ttt cta gcc tgc    270
Phe Tyr His Lys Thr Asn Ile Lys Met His Cys Glu Phe Leu Ala Cys
     25                  30                  35 tgg cct gcc ttc act gtc ctg ggg gag gct tgg aga gac cag gtg gac    318
Trp Pro Ala Phe Thr Val Leu Gly Glu Ala Trp Arg Asp Gln Val Asp
 40                  45                  50                  55 tgg agt ata ctg ttg aga gac gct ggt ctg gtg aag atg tcc agg aaa    366
Trp Ser Ile Leu Leu Arg Asp Ala Gly Leu Val Lys Met Ser Arg Lys
             60                  65                  70 cca cga gcc tcc agc cca ttg tcc aac aac cac cca cca aca cca aag    414
Pro Arg Ala Ser Ser Pro Leu Ser Asn Asn His Pro Pro Thr Pro Lys
                 75                  80                  85 agg ttc cca aga caa ctc gga agg gaa aag gga ccc atc gag gaa gtt    462
Arg Phe Pro Arg Gln Leu Gly Arg Glu Lys Gly Pro Ile Glu Glu Val
                     90                  95                 100 cca gga aca aaa ggc tct cca taaaagaccg ccgcttcaaa aaaacctgag       513
Pro Gly Thr Lys Gly Ser Pro
             105                 110 gaatggagtg ggccaacact atccagccac tctgaccagc cgaacgagga actcaatcaa    573
aatgagccat agcgggacca caagggcaag gagaccacca ctttctccag tctcttttcg    633
gacagccagt aattcccggg caaggccaga gacttcaagt ctatctgaaa agtctccaga    693
ggtctaaccc cagataaata gccaacaggg tgtagagtac gttttacacc ccaaagggta    753
tgccccatgt gatggaaata aaatgaacat gttgtaaaaa aaaaa                    799
```

<210> SEQ ID NO 2
<211> LENGTH: 110
<212> TYPE: PRT
<213> ORGANISM: Homo sapiens

<400> SEQUENCE: 2

```
Met Trp Met Gly Leu Ile Gln Leu Val Glu Gly Val Lys Arg Lys Asp
  1               5                  10                  15

Gln Gly Phe Leu Glu Lys Glu Phe Tyr His Lys Thr Asn Ile Lys Met
             20                  25                  30

His Cys Glu Phe Leu Ala Cys Trp Pro Ala Phe Thr Val Leu Gly Glu
         35                  40                  45

Ala Trp Arg Asp Gln Val Asp Trp Ser Ile Leu Leu Arg Asp Ala Gly
     50                  55                  60

Leu Val Lys Met Ser Arg Lys Pro Arg Ala Ser Ser Pro Leu Ser Asn
 65                  70                  75                  80

Asn His Pro Pro Thr Pro Lys Arg Phe Pro Arg Gln Leu Gly Arg Glu
                 85                  90                  95

Lys Gly Pro Ile Glu Glu Val Pro Gly Thr Lys Gly Ser Pro
            100                 105                 110
```

<210> SEQ ID NO 3
<211> LENGTH: 850
<212> TYPE: DNA
<213> ORGANISM: Homo sapiens -continued

```
<400> SEQUENCE: 3
gtgcaattgc tagtactatg tgtcaacttg tctaggctat actgctcagc tgtgtggtca      60
aacagtagtc tagatgttgc tgtgaaggta ttttgtagat gtgatcaaca tttacaatca     120
gttgatttta agtaaagcag tttaacttcc aatatgtgga tgggcctcat ccaattagtt     180
gaaggtgtta agagaaaaga ccaaggtttc ctggaaaagg aattctacca caagactaac     240
ataaaaatgc actgtgagtt tcatgcctgc tggcctgcct tcactgtcct ggggggaggct    300 tggagagacc aggtggactg gagtatactg ttgagagacg ctggtctggt gaagatgtcc     360
aggaaaccac gagcctccag cccattgtcc aacaaccacc caccaacacc aaagaggcga     420
ggaagtggaa ggcatcctct caaccctggc ccagaagccc tatcaaagtt cccaagacaa     480
ctcggaaggg aaaagggacc catcgaggaa gttccaggaa caaaaggctc tccataaaag     540
accgccgctt caaaaaaacc tgaggaatgg agtgggccaa cactatccag ccactctgac     600
cagccgaacg aggaactcaa tcaaaatgag ccatagcggg accacaaggg caaggagacc     660
accactttct ccagtctctt ttcggacagc cagtaattcc cgggcaaggc cagagacttc     720
aagtctatct gaaaagtctc cagaggtcta accccagata aatagccaac agggtgtaga    780
gtacgtttta caccccaaag ggtatgcccc atgtgaggga aataaaatga acatgttgta    840
aaaaaaaaaa                                                            850

<210> SEQ ID NO 4
<211> LENGTH: 127
<212> TYPE: PRT
<213> ORGANISM: Homo sapiens

<400> SEQUENCE: 4

Met Trp Met Gly Leu Ile Gln Leu Val Glu Gly Val Lys Arg Lys Asp
  1               5                  10                  15

Gln Gly Phe Leu Glu Lys Glu Phe Tyr His Lys Thr Asn Ile Lys Met
             20                  25                  30

His Cys Glu Phe His Ala Cys Trp Pro Ala Phe Thr Val Leu Gly Glu
         35                  40                  45

Ala Trp Arg Asp Gln Val Asp Trp Ser Ile Leu Leu Arg Asp Ala Gly
     50                  55                  60

Leu Val Lys Met Ser Arg Lys Pro Arg Ala Ser Ser Pro Leu Ser Asn
 65                  70                  75                  80

Asn His Pro Pro Thr Pro Lys Arg Arg Gly Ser Gly Arg His Pro Leu
                 85                  90                  95

Asn Pro Gly Pro Glu Ala Leu Ser Lys Phe Pro Arg Gln Leu Gly Arg
            100                 105                 110

Glu Lys Gly Pro Ile Glu Glu Val Pro Gly Thr Lys Gly Ser Pro
        115                 120                 125
```

TAXOL RESISTANCE ASSOCIATED GENE

CROSS-REFERENCE TO RELATED APPLICATION

This application claims benefit from U.S. provisional application Ser. No. 60/079,771, filed Mar. 27, 1998.

BACKGROUND OF THE INVENTION

Acquired drug resistance to currently available chemotherapeutic drugs is a major cause of failure of cancer treatment (Gottesman et al., 1993, Annu Rev. Biochem 62:385–427; Van Der Zee et al., 1995, Gynecologic Oncol. 58:165–178; Casazza et al., 1996, Cancer Treat. Res. 87:1–171). Many of the most common carcinomas, including breast and ovarian cancer, are initially relatively sensitive to a wide variety chemotherapy agents. However, acquired drug resistance phenotype typically occurs after months or years of exposure to chemotherapy. Determining the molecular basis of drug resistance may offer opportunities for improved diagnostic and therapeutic strategies.

Taxol is a natural product derived from the bark of *Taxus brevafolio* (Pacific yew). Taxol inhibits microtubule depolymerization during mitosis and results in subsequent cell death. Taxol displays a broad spectrum of tumorcidal activity including against breast, ovary and lung cancer (McGuire et al., 1996, *N. Engld. J. Med.* 334:1–6; and Johnson et al., 1996, *J. Clin. Ocol.* 14:2054–2060). While taxol is often effective in treatment of these malignancies, it is usually not curative because of eventual development of taxol resistance. Cellular resistance to taxol may include mechanisms such as enhanced expression of P-glycoprotein and alterations in tubulin structure through gene mutations in the β chain or changes in the ratio of tubulin isomers within the polymerized microtubule (Wahl et al., 1996, *Nature Medicine* 2:72–79; Horwitz et al., 1993, *Natl. Cancer Inst.* 15:55–61; Haber et al., 1995, *J. Biol. Chem.* 270:31269–31275; and Giannakakou et al., 1997, *J. Biol. Chem.* 272:17118–17125). Some tumors acquires taxol resistance through unknown mechanisms.

SUMMARY OF THE INVENTION

Figure 3:
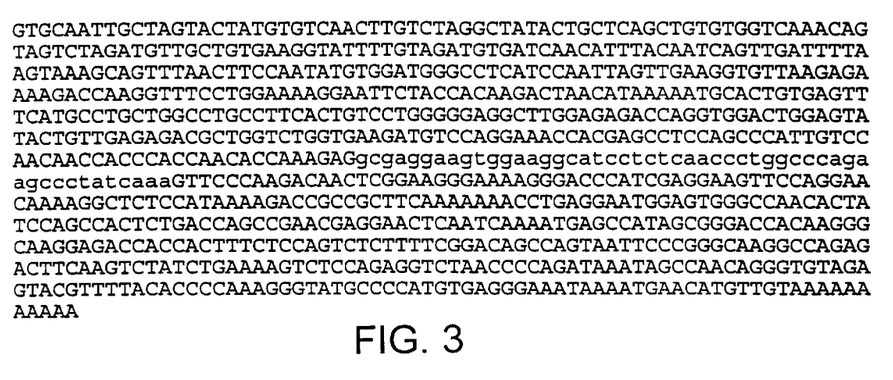
FIG. 3 is the sequence (SEQ ID NO:3) of a full-length TRAG-3β cDNA.
Figure 4:
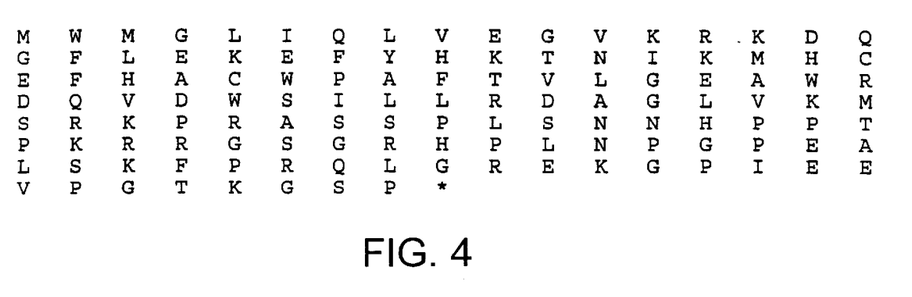
FIG. 4 is the amino acid sequence (SEQ ID NO:2) of the TRAG-3β polypeptide.

A gene that is overexpressed in taxol-resistant cancer cell lines has now been discovered and characterized. The gene is designated Taxol Resistance Associated Gene-3 ("TRAG-3"). At least two alternatively spliced forms of TRAG-3, referred to herein as TRAG-3α and TRAG-3β, exist. The TRAG-3α cDNA sequence shown in FIG. 2 encodes a 110 amino acid protein. The TRAG-3β cDNA shown in FIG. 3 encodes a 127 amino acid protein (FIG. 4). TRAG-3 is expressed predominantly in chemotherapy resistant cell lines and the majority of melanoma cell lines and melanoma malignant tissues. It is minimally, if at all, expressed in normal cells and tissues. As used herein, the term TRAG-3 refers to any and all TRAG-3 gene products. The TRAG-3 gene product, i.e., the TRAG-3 polypeptide, modulates expression of several genes involved in taxol resistance displayed by mammalian cells.

Based on the discoveries, the invention features an isolated nucleic acid containing a nucleotide sequence that encodes a polypeptide that shares at least 80% sequence identity with SEQ ID NO:2 or SEQ ID NO:4. Preferably, it shares at least 90% sequence identity with SEQ ID NO:2 or SEQ ID NO:4, and more preferably, it shares at least 95% sequence identity with SEQ ID NO:2 or SEQ ID NO:4. Alternatively, the nucleotide sequence defines a DNA molecule whose complement hybridizes under stringent hybridization conditions to a DNA molecule having a sequence consisting of SEQ ID NO:1 or SEQ ID NO:3.

The invention also includes an isolated nucleic acid (antisense) that hybridizes under stringent hybridizaton conditions to a nucleic acid whose nucleotide sequence is the complement of SEQ ID NO:1 or SEQ ID NO:3.

The invention also includes an isolated nucleic acid containing a nucleotide sequence that encodes: SEQ ID NO:2; SEQ ID NO:4; SEQ ID NO:2 with one or more conservative amino acid substitutions; or SEQ ID NO:4 with one or more conservative amino acid substitutions. In some embodiments, the nucleotide sequence is SEQ ID NO:1 or SEQ ID NO:3.

Preferably, the polypeptide modulates expression of at least one gene involved in taxol resistance displayed by a mammalian cell. Examples of genes involved in taxol resistance include: annexin I, interleukin 6 (IL-6), interleukin 8 (IL-8), macrophage inflammatory protein 2α, and natural killer cell enhancing factor B (NKEFB).

The invention also includes a vector containing an above-described nucleic acid. In the vector, the nucleic acid can be operably linked to at least one expression control sequence. The invention also includes a cell comprising the vector.

The invention also includes a substantially pure polypeptide that has an amino acid sequence sharing at least 80% sequence identity with SEQ ID NO:2 or SEQ ID NO:4. The invention also includes a substantially pure polypeptide whose amino acid sequence is: SEQ ID NO:2; SEQ ID NO:4, SEQ ID NO:2 with one or more conservative amino acid substitutions; or SEQ ID NO:2 with one or more conservative amino acid substitutions. Preferably, the polypeptide modulates expression of at least one gene involved in taxol resistance displayed by a mammalian cell, e.g., annexin I, IL-6, IL-8, macrophage inflammatory protein 2α, and NKEFB.

The invention also includes an antibody that binds to a TRAG-3 polypeptide. Preferably, the antibody binds specifically to a TRAG-3 polypeptide, or a biologically active portion thereof. The antibody can be a monoclonal, polyclonal, or engineered antibody. The antibody is useful in detecting a TRAG-3 polypeptide, e.g., in a biological sample, or to alter the activity of TRAG-3.

The invention also includes a method for modulating expression of annexin I, IL-6, IL-8, macrophage inflammatory protein 2α, or NKEFB, in a mammalian cell. The method includes introducing into the cell a vector containing a TRAG-3 coding sequence operably linked to expression control sequences.

The invention also includes a screening method for identifying a compound that inhibits expression of a TRAG-3 gene in a cell. The method includes: (a) providing a treatment test cell and a control test cell, both of which express endogenous TRAG-3, (b) contacting the treatment test cell with a candidate compound, and (c) detecting a decrease in the level of TRAG-3 gene expression in the treatment test cell, compared to the level of TRAG-3 gene expression in the control test cell. The test cell can be a taxol-resistant mammalian cancer cell that overexpresses endogenous TRAG-3 as compared to a non-taxol-resistant cancer cell from a parental cell line. The decrease in the expression level of TRAG-3 gene expression can be detected through measurement of TRAG-3 RNA level in the cell, or through measurement of TRAG-3 polypeptide level in the cell. TRAG-3 polypeptide level can be measured by means of a TRAG-3 antibody.

The invention also includes a screening method for identifying a compound that inhibits the biological activity of a TRAG-3 polypeptide in a cell. The method includes: (a) providing a treatment test cell and a control test cell, both of which: (1) contain a TRAG-3 coding sequence operably linked to expression control sequences, and (2) express an endogenous gene whose expression is upregulated by a TRAG-3 polypeptide; (b) contacting the treatment test cell with a candidate compound; and (c) detecting a decrease in the expression level of the endogenous gene in the treatment test cell, compared to the expression level of the endogenous gene in the control test cell. The level of TRAG-3-modulated gene expression can be measured according to TRAG-3 RNA level or TRAG-3 polypeptide level. The endogenous gene whose expression is upregulated by a TRAG-3 polypeptide can be an annexin I gene, IL-6 gene, IL-8 gene, or macrophage inflammatory protein 2α gene.

The invention also includes a screening method for identifying a compound that inhibits the biological activity of a TRAG-3 polypeptide in a cell. The method includes: (a) providing a treatment test cell and a control test cell, both of which contain: (1) a TRAG-3 coding sequence operably linked to expression control sequences, and (2) a reporter gene operably linked to a positive expression control sequence naturally associated with an endogenous gene whose expression is upregulated by a TRAG-3 polypeptide; (b) contacting the test cell with a candidate compound; and (c) detecting a decrease in the level of reporter gene expression in the treatment test cell, compared to the level of reporter gene expression in the control test cell.

The invention also includes a screening method for identifying a compound that inhibits the biological activity of a TRAG-3 polypeptide in a cell. The method includes: (a) providing a treatment test cell and a control test cell, both of which: (1) contain a TRAG-3 coding sequence operably linked to expression control sequences, and (2) express an endogenous gene whose expression is downregulated by a TRAG-3 polypeptide; (b) contacting the treatment test cell with a candidate compound, and (c) detecting an increase in the expression level of the endogenous gene in the treatment test cell, compared to the expression level of the endogenous gene in the control test cell. The endogenous gene whose expression is downregulated by a TRAG-3 polypeptide can be an NKEFB gene.

The invention includes an additional screening method for identifying a compound that inhibits the biological activity of a TRAG-3 polypeptide in a cell. The method includes: (a) providing a treatment test cell and a control test cell, both of which: (1) contain a TRAG-3 coding sequence operably linked to expression control sequences, and (2) a reporter gene operably linked to a negative expression control sequence naturally associated with an endogenous gene whose expression is downregulated by a TRAG-3 polypeptide; (b) contacting the test cell with a candidate compound; and (c) detecting an increase in the expression level of the reporter gene in the treatment test cell, compared to the expression level of the reporter gene expression in the control test cell.

The invention also includes a method for identifying a cancer tissue suitable for treatment with a compound that inhibits TRAG-3 gene expression or that inhibits the biological activity of a TRAG-3 polypeptide. The method includes: (a) providing a sample of the cancer tissue, and (b) detecting TRAG-3 gene expression in the sample.

The present invention also provides a diagnostic assay for identifying whether a cell is cancerous. The method includes: (a) providing a cell which is suspected of being cancerous and (b) determining whether the cell expresses TRAG-3. Expression of TRAG-3 is an indication that the cell is cancerous. TRAG-3 gene expression can be detected through measurement of TRAG-3 RNA level in the cell, or through measurement of TRAG-3 polypeptide level in the cell.

As used herein, "a substantially pure TRAG-3 polypeptide" or "purified" or "isolated" means a TRAG-3 polypeptide separated from components that naturally accompany it. Typically, the protein is substantially pure when it is at least 60%, by weight, free from the proteins and other naturally-occurring organic molecules with which it is naturally associated. Preferably, the purity of the preparation is at least 75%, more preferably at least 90%, and most preferably at least 99%, by weight. A substantially pure TRAG-3 polypeptide can be obtained, for example, by extraction from a natural source, by expression of a recombinant nucleic acid encoding a TRAG-3 polypeptide, or by chemical synthesis. Purity can be measured by any appropriate method, e.g., column chromatography, polyacrylamide gel electrophoresis, or HPLC analysis. A chemically synthesized protein or a recombinant protein produced in a cell type other than the cell type in which it naturally occurs is, by definition, substantially free from components that naturally accompany it. Accordingly, substantially pure proteins include those having sequences derived from eukaryotic organisms but synthesized in *E. coli* or other prokaryotes.

As used herein, "high stringency" means the following nucleic acid hybridization and wash conditions: hybridization at 42° C. in the presence of 50% formamide; a first wash at 65° C. with 2×SSC containing 1% SDS; followed by a second wash at 65° C. with 0.1×SSC.

As used herein, "isolated DNA" means DNA free of the genes that flank the gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Also included is a recombinant DNA that includes a portion of SEQ ID NO:1 and that encodes an alternative splice variant of RKLF.

As used herein, "operably linked" means incorporated into a genetic construct so that expression control sequences effectively control expression of a gene of interest.

As used herein, "polypeptide" means any peptide-linked chain of amino acids, regardless of length or post-translational modification, e.g., glycosylation or phosphorylation.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence of 10 nucleotides in length are identical to the corresponding positions in a second 10-nucleotide sequence, then the two sequences have 70% sequence identity. Preferably, the length of the compared sequences is at least 60, more preferably at least 75, and most preferably, at least 100 nucleotides or amino acid residues.

In the case of polypeptide sequences that are less than 100% identical to a reference sequence, the non-identical positions are preferably, but not necessarily, conservative substitutions for the reference sequence. Conservative substitutions include substitutions within the following groups, e.g., glycine and alanine; valine, isoleucine, and leucine; aspartic acid and glutamic acid; asparagine and glutamine; serine and threonine; lysine and arginine; and phenylalanine and tyrosine.

Sequence identity can be measured using sequence analysis software (e.g., the Sequence Analysis Software Package of the Genetics Computer Group, University of Wisconsin Biotechnology Center, 1710 University Avenue, Madison, Wis. 53705) with the default parameters as specified therein. BLAST software, provided as a service by the National Center for Biotechnology Information is useful for making sequence comparisons. The programs are described in detail by Karlin et al., (*Proc. Natl. Acad. Sci. USA* 87:2264–68, 1990 and 90:5873–7, 1993) and Altschul et al., (*Nucl. Acids Res.* 25:3389–3402, 1997), and they are available on the internet Unless otherwise defined, all technical and scientific terms used herein have the same meaning as commonly understood by one of ordinary skill in the art to which this invention belongs. Exemplary methods and materials are described below, although methods and materials similar or equivalent to those described herein can be used in the practice or testing of the present invention. All publications mentioned herein are incorporated by reference, in their entirety. In case of conflict, the present specification, including definitions, will control. The materials, methods, and examples are illustrative only and not intended to be limiting.

Other features and advantages of the invention will be apparent from the following detailed description, and from the claims.

DETAILED DESCRIPTION

Several taxol-resistant human cancer cell lines were established through incremental exposure of taxol-sensitive parental cells to increasing taxol concentrations. A full-length, human TRAG-3α cDNA was identified from one of these taxol-resistant cell lines by using the differential display technique, essentially as described by Liang et al. (Science 257:967–971, 1992; *Nucleic Acids Res.* 21:3269–3275, 1993). TRAG-3α is expressed in taxol-resistant cancer cells. The deduced 110 amino acid sequence (SEQ ID NO:2) encoded by the human TRAG-3α CDNA shares no significant homology to known proteins.

Taxol-resistant cancer cells and other cancerous cell lines, e.g., melanoma cell lines, were also observed to express a splice variant, TRAG-3β. The TRAG-3β cDNA is shown in FIG. 3 and encodes a protein of 127 amino acids (FIG. 4). As used herein, TRAG-3 includes any and all of TRAG-3 gene products.

Evidence that TRAG-3 is a drug resistance associated gene includes the observation that this gene is also overexpressed in the taxol resistant breast cancer line MDA $435_{TR}$ and the doxorubicin resistant multiple myeloma lines 8226/$DOX_{40}$ and 8226/$NMR_{10}V$ as compared to their drug sensitive parent lines.

The lack of significant TRAG-3 expression in normal tissues and the marked overexpression of this gene in approximately half of the tumor cell lines evaluated indicates that TRAG-3 is also linked in some cases, to the malignant phenotype. Expression of this gene in tumor cell lines is broad, and includes carcinomas, myeloid and lymphoid malignancies, as well prostate cancers which are intrinsically drug resistant. In particular, TRAG-3 was expressed in nearly 80% of the melanoma cell lines evaluated, and in 100% of the malignant melanoma tumors. Since TRAG-3 is expressed in a large array of tumor cell lines, it indicates that TRAG-3 does not act through a highly specialized lineage specific pathway. Although the gene was isolated from a taxol resistant cell line that overexpresses the MDR-1 gene, TRAG-3 expression in several other cell lines demonstrates that the expression is not tightly linked to MDR expression. The reversal of taxol drug resistance in SKOV-$3_{TR}$ with verapamil and the failure of TRAG-3 transfectants to change taxol sensitivity shows that this gene does not directly induce taxol resistance.

A TRAG-3 antagonist, i.e., an agent that inhibits TRAG-3 gene expression or the activity of a TRAG-3 polypeptide, can be administered therapeutically. It can be administered in combination with taxol or another chemotherapeutic agent, e.g., vincristin, to treat a taxol-resistant cancer. Examples of TRAG-3 antagonists include a TRAG-3 antisense molecule, a TRAG-3 antibody, a monomeric organic molecule, and an inactivated, e.g., truncated, TRAG-3 polypeptide that binds to TRAG-3 binding sites in vivo, thereby acting as a competitive inhibitor of active, endogenous TRAG-3.

Nucleic Acids Encoding TRAG-3 Polypeptides

Nucleic acids encoding a homolog of SEQ ID NO:2 or SEQ ID NO:4 are within the scope of the invention. A homolog of SEQ ID NO:2 or SEQ ID NO:4 shares at least 50%, 60%, 70%, or 80% sequence identity with SEQ ID NO:2 or SEQ ID NO:4. Polypeptides having the sequence of SEQ ID NO:2, SEQ ID NO:4 or a homolog thereof are collectively termed TRAG-3 polypeptides. TRAG-3 polypeptides include, but are not limited to, TRAG-3 from non-human mammalian species, human variants of SEQ ID NO:2 or SEQ ID NO:4 that arise due to splicing, polymorphism, or mutants of any of the naturally occurring TRAG-3 polypeptide sequences.

TRAG-3 polypeptides can regulate the expression of other proteins such as zinc finger proteins, IL-6, IL-8, macrophage inflammatory protein 2α, and NKEFB. In addition, naturally occurring TRAG-3 polypeptides are overexpressed in taxol-resistant cancer cells, and therefore can serve as a target for cancer chemotherapy.

Nucleic acids encoding TRAG-3 polypeptides can be selected by the ability to hybridize under stringent conditions to a probe containing all or part of SEQ ID NO:1 or SEQ ID NO:3. By way of example, DNA encoding a mouse TRAG-3 polypeptide can be isolated by screening a mouse cDNA or genomic library with a TRAG-3 probe (e.g., a complementary fragment of SEQ ID NO:1 or SEQ ID NO:3). See the following section for more detailed description of useful probes.

Typically, hybridization conditions initially used to identify related sequences are of low to moderate stringency. After hybridization, the nucleic acids are washed to dissociate duplexes that are bound together by some non-specific interaction. The stringency used in washing is typically higher than that used in hybridization. In general, it is desirable to increase the washing stringency when the degree of homology between the target nucleic acid and the probe sequence is expected to be high. Stringency-affecting parameters include, primarily, temperature and salt concentration. In general, the lower the salt concentration and the higher the temperature, the higher the stringency. Washing can be initiated at a low temperature (e.g., room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

An example of a progression from lower to higher stringency conditions is the following, where the salt content is given as the concentration of a sodium citrate/sodium chloride solution ("SSC") for salt content of 20×SSC, see Sambrook et al., 1989, *Molecular Cloning, A Laboratory Manual*, 2nd Ed. Cold Spring Harbor Laboratory Press, Cold Spring Harbor, N.Y.). Nucleic acid molecules are hybridized at 42° C. in 2×SSC/0.1% sodium dodecylsulfate ("SDS") and then washed in 0.2×SSC/0.1% SDS at room temperature (for conditions of low stringency); in 0.2×SSC/0.1% SDS at 42° C. (for conditions of moderate stringency); and in 0.1×SSC at 68° C. (for conditions of high stringency). Washing can be carried out using only one of the conditions given, or each of the conditions can be used for, e.g., 10–15 minutes each in the order listed above. Any or all of the washes can be repeated.

Once a nucleic acid hybridizable by a TRAG-3 probe is detected, the nucleic acid is isolated by any of a number of standard techniques. The sequence of the nucleic acid is then determined. The amino acid sequence encoded by the nucleic acid can be deduced and compared to SEQ ID NO:2. If the deduced amino acid sequence shares at least 80% identity with SEQ ID NO:2, the polypeptide encoded by the nucleic acid is a TRAG-3 polypeptide.

Nucleic acids of the invention can form part of a hybrid gene encoding additional polypeptide sequences, for example, sequences that function as a marker (e.g., the FLAG™ sequence, E-tag, c-myc tag, and HA tag) or reporter (e.g., β-lactamase, chloramphenicol acetyltransferase, adenosine deaminase, aminoglycoside phosphotransferase, dihydrofolate reductase, hygromycin-B-phosphotransferase, thymidine kinase, β-galactosidase, and xanthine guanine phosphoribosyltransferase).

Nucleic Acids Hybridizable by TRAG-3 Probes

SEQ ID NO:1 or SEQ ID NO:3 can be used as probes to identify nucleic acids related to a human TRAG-3 gene. Fragments of SEQ ID NO:1 or SEQ ID NO:3 and sequences complementary to SEQ ID NO:1, SEQ ID NO:3, or parts thereof, can be used as probes also, so long as they are at least 10, and preferably at least 15 (e.g., 18, 20, 25, 50, 100, 150, or 200 nucleotides), nucleotides in length. TRAG probes can be produced using any of several standard methods (see, e.g., Ausubel et al., 1989, *Current Protocols in Molecular Biology*, Vol. I, Green Publishing Associates, Inc., and John Wiley & Sons, Inc., N.Y.). For example, the probe can be generated using PCR amplification methods in which oligonucleotide primers are used to amplify a portion of SEQ ID NO:1 or SEQ ID NO:3 that can be used as a specific probe. Such probes are part of the invention.

Hybridization is carried out under stringent conditions. One exemplary set of stringent conditions are those under which hybridization is carried out at 50° C. in Church buffer (7% SDS, 0.5% NaHPO$_4$, 1 M EDTA, 1% bovine serum albumin ("BSA")) and washing is carried out at 50° C. in 2×SSC.

Nucleic acids hybridizable by the above-described probes under stringent conditions can be used as probes themselves to analyze the expression of TRAG-3 polypeptides in cancer cells. These nucleic acids can also be used to express TRAG-3 polypeptides or immunogenic fragments thereof for raising TRAG-3 antibodies. The nucleic acids hybridizable by the TRAG-3 probes may also encode dominant negative mutants of TRAG-3, and can therefore be introduced into taxol-resistant cancer cells to effect inhibition of the functions of endogenous TRAG-3.

Genomic fragments of the TRAG-3 locus that are hybridizable by the above-described probes are also included in the invention. Such fragments are useful starting materials for generating, e.g., knockout constructs that are used to create non-human transgenic mammals containing null mutations at the TRAG-3 locus.

TRAG-3 Antisense Molecules

TRAG-3 antisense molecules can be used to inhibit in vivo translation of TRAG-3 RNA, thereby inhibiting TRAG-3 polypeptide production in vivo. Any of various known methods for introducing nucleic acids into mammalian tissues can be used. Cells in intact tissue take up naked DNA. For example, mammalian muscle cells have been shown to take up naked DNA dissolved in aqueous solution and injected into muscle tissue. Alternatively, however, TRAG-3 antisense molecules can be introduced into mammalian tissues by means of a vector, (e.g., a retrovirus, see also below) or vehicle (e.g., liposomes) to improve uptake efficiency. The selection and use of a suitable vector or vehicle for introducing TRAG-3 DNA into mammalian tissues is within ordinary skill in the art.

Direct transfer of TRAG-3 DNA into intact mammalian cancer cells, can be carried out by means of cationic lipids (Lim et al., 1991, *Circulation* 83:2007–2011; Lynch et al., 1992, *Proc. Natl. Acad. Sci. USA* 89:1138–1142; and Flugelman et al., 1992, *Circ. Res.* 70:348–354). An exemplary cationic lipid is commercially available as Lipofectin™

(GIBCO/BRL). Another commercial lipid for introduction of DNA into cells is Liposin™.

Expression Control Sequences and Vectors

Various uses of the TRAG-3 nucleic acids of this invention will involve cloning of TRAG-3 sequences into a vector, where they are operably linked to one or more expression control sequences. The need for, and identity of, expression control sequences will vary according to the type of cell in which the TRAG-3 sequence is to be expressed. Examples of expression control sequences include transcriptional promoters, enhancers, suitable mRNA ribosomal binding sites, and sequences that terminate transcription and translation. Suitable expression control sequences can be selected by one of ordinary skill in the art. Standard methods can be used by the skilled person to construct expression vectors. See, generally, Sambrook et al., 1989, *Cloning—A Laboratory Manual* (2nd Edition), Cold Spring Harbor Press.

Vectors useful in this invention include plasmid vectors and viral vectors. Viral vectors can be those derived from retroviruses, adenovirus, adeno-associated virus, SV40 virus, or herpes viruses. Once introduced into a host cell (e.g., bacterial cell, yeast cell, avian cell, mammalian cell), the vector can remain episomal, or be incorporated into the genome of the host cell.

In bacterial systems, a number of expression vectors may be advantageously selected depending upon the use intended for the gene product being expressed. For example, when a large quantity of such a protein is to be produced, e.g., for studying the interaction of a TRAG-3 polypeptide with other proteins or for raising antibodies to the polypeptide, a vector capable of directing the expression of high levels of a fusion protein (e.g., a GST fusion protein) that is readily purified may be desirable. In general, such fusion proteins are soluble and can easily be purified from lysed cells by adsorption to, e.g., glutathione-agarose beads followed by elution in the presence of free glutathione.

In mammalian host cells, a number of viral-based expression systems can be utilized. In cases where TRAG-3 antisense sequences are to be introduced to a patient to inhibit growth of cancer cells, vectors that primarily target fast-proliferating cells may be preferred. Retroviral vectors are particularly useful, as they seletively integrate into the genome of replicating cells, such as tumor cells.

TRAG-3 Polypetides

A TRAG-3 polypeptide can be isolated and purified from a natural source. Alternatively, it can be produced recombinantly or chemically synthesized by conventional methods. A TRAG-3 polypeptide, full-length or truncated, can also be part of a fusion protein.

The TRAG-3 polypeptides can be prepared for a variety of uses, e.g., generation of antibodies, and identification of other cellular gene products or exogenous compounds that can modulate the expression of the TRAG-3 gene or the activity of the TRAG-3 protein in cancer cells.

Techniques for generating substantially polypeptide preparations are well known in the art. A typical method involves transfecting host cells (e.g., bacterial cells, mammalian cells, or plant cells) with an expression vector carrying a nucleic acid that encodes a TRAG-3 polypeptide of interest. The recombinant polypeptide so produced can be purified from the culture medium or from lysates of the cells.

Conventional site-directed mutagenesis techniques can be applied to a TRAG-3 coding sequence, e.g., SEQ ID NO:1, to generate TRAG-3 sequence variants optimized for expression in a given type of host cell. For example, N-linked glycosylation sites can be altered or eliminated to achieve expression of a homogeneous product that is more easily recovered and purified from yeast hosts that hyperglycosylate N-linked sites. See Miyajima et al., 1986, *EMBO J.* 5:1193.

TRAG-3 Antibodies

A TRAG-3 antibody of the invention can be a polyclonal antibody, a monoclonal antibody, or an engineered derivative of a monoclonal antibody. Polyclonal and monoclonal antibody production, and monoclonal antibody engineering, are within ordinary skill in the art. Uses of TRAG-3 antibodies include inhibiting the activity of TRAG-3 polypeptides, detecting TRAG-3 polypeptides in immunohistochemical methods and immunoassays, and purifying TRAG-3 polypeptides.

The invention encompasses not only an intact monoclonal antibody, but also an immunologically active antibody fragment. Examples of such a fragment include a Fab or $(Fab)_2$ fragment, an engineered single chain Fv molecule, and a chimeric antibody (such as a "humanized" antibody). Typically, a chimeric antibody includes a variable region of a non-human antibody, e.g., a murine variable region, and a constant region of a human antibody.

In some embodiments of the invention, an antibody or antibody fragment is linked to a detectable label. Examples of detectable labels include a radioactive label, a non-radioactive isotopic label, a fluorescent label, an enzyme label, and a calorimetric label.

Screening Assays

The invention also encompasses methods for identifying compounds that modulate the expression of a TRAG-3 gene or the activity of a TRAG-3 polypeptide. Candidate compounds that can be screened in accordance with the invention include nucleic acids, polypeptides, oligopeptides, antibodies, and monomeric organic compounds that bind to TRAG-3 and decrease activity.

To screen for compounds that inhibit the expression of TRAG-3 genes, test cells that overexpress endogenous TRAG-3 are preferred. Useful cells include taxol-resistant cancer cells that overexpress TRAG-3. Such cells can be obtained as described below.

To screen for compounds that inhibit the activity of TRAG-3 polypeptides, cells that express either the endogenous TRAG-3 or a recombinant TRAG-3 polypeptide can be used. The latter cells can be obtained by transfecting host cells with an expression vector containing a TRAG-3 coding sequence operably linked to suitable expression control sequences. The recombinant TRAG-3 polypeptide expressed in the test cell typically will display one or more of the biological functions (e.g., transcriptional regulation activity) displayed by human TRAG-3. Human TRAG-3 upregulates the expression of annexin I, IL-6, IL-8, and macrophage inflammatory protein $2\alpha$, while downregulating the expression of NKEFB. Thus, the relative expression levels of these proteins as compared to untreated controls can be used to indicate the activity of a TRAG-3 polypeptide in screening assays.

Expression levels of a TRAG-3-regulated gene can be measured by conventional Northern or Western blot analysis. A decrease in the expression level of, e.g., IL-6, IL-8, annexin I, and macrophage inflammatory protein $2\alpha$, or an increase in the expression level of NKEFB, indicates that the candidate compound inhibits the biological activity of the endogenous TRAG-3 polypeptide in the test cell.

Cell Culture and Selection of Taxol-Resistant Cells

Human ovarian cancer cell line SKOV-3 and other cancer cell lines were obtained from the *American Type Culture Collection* (Rockville, Md.). Human multiple myeloma doxorubicin-resistant cell lines 8226/$DOX_{40}$ and 8226/$NMR_{10}V$ and their sensitive counterpart 8226/S were provided by Dr. William S. Dalton at University of South Florida, H. Lee Moffitt Cancer Center (see also Abbaszadegan et al., 1996, Int. *J. Cancer* 66:506–514). The NCI Cancer Cell Line Panel was provided by Dr. Anne Monks at the National Cancer Institute ("NCI"). β-tubulin mutant ovarian carcinoma cell lines PTX 10 and PTX 22 and their sensitive parental line 1A9 were kindly provided by Dr. Tito Fojo (Giannakakou et al., 1997, *J. Biol. Chem.* 272:17118–17125). SKOV-3 and SKOV-$3_{TR}$ were grown in RPMI 1640 supplemented with 10% fetal bovine serum ("FBS"), 100 units/ml penicillin, and 100 μg/ml streptomycin (GIBCO, Grand Island, N.Y.). Cells were incubated at 37° C. in 5% $CO_2$ atmosphere and passaged once every 3 days. SKOV-$3_{TR}$ was selected from SKOV-3 by stepwise increases in taxol concentrations from 0.0001 μM to 0.3 μM.

Many of the melanoma cell lines were kindly donated by Dr. Hensin Tsao (Massachusetts General Hospital, Boston, Mass.). Lines were cultured in Dulbecco's Modified Eagle Medium supplemented with 20% FBS, penicillin and streptomycin at 100 units/ml and 100 g/ml, respectively (Gibco, Grand Island, N.Y.). Cells were incubated in 5% CO2 and 95% air atmosphere at 37° C., and passaged twice every six days.

The four metastatic malignant melanoma tumors used in this study were obtained from the Massachusetts General Hospital Tumor Bank (Boston, Mass.). Specimens were frozen soon after surgical removal in liquid nitrogen and stored in liquid nitrogen until RNA isolation.

All drugs were obtained from commercial sources. In vitro cytotoxicity was measured using a tetrazolium-based semi-automated calorimetric assay (i.e., MTT assay), as described (Carmichael et al., 1987, *Cancer Res.* 47:936–942). Briefly, 2×$10^3$ cells per well were cultured for 6 days with taxol or with taxol plus 30 μM verapamil. 20 μl of 5 mg/ml MTT solution was added to each well and incubated for 4 hours. $A_{590\ nm}$ was measured after MTT formazan was solubilized with HCl-isopropanol solution. The absorbance values were normalized by assigning the value of the parent line in media to 1.0 and the value of the no-cell blank to 0. Experiments were performed in duplicate.

RNA Isolation and Differential Disilay

Total RNA was extracted from cells using TRIZOL™ REAGENT (GIBCO, Grand Island, N.Y.) according to the manufacturer's instructions. DNA in the samples was removed by treatment with RNase-free DNase (Boehringer Mannheim, Indianapolis, Ind.). Differential display was performed as described (Liang et al., 1992, *Science* 257:967–971) with use of the RNAIMAGE kit (Genhunter, Nashville, Tenn.). Briefly, 0.2 μg of total RNA from a cell, e.g., SKOV-3 and SKOV-$3_{TR}$ cells, were reverse-transcribed with H-$T_{11}$M (M=A, G or C) primers. Polymerase chain reaction ("PCR") was performed using the corresponding H-$T_{11}$M primer and an arbitrary primer. The PCR consisted of (i) 40 cycles of denaturation at 94° C. for 30 seconds, annealing at 40° C. for 2 minutes, and primer extension at 72° C. for 30 seconds; and (ii) 1 final cycle of extension at 72° C. for 7 minutes. 3.5 μl of PCR products was mixed with 1 μl of loading dye and heated at 80° C. for 2 minutes immediately before being loaded onto a 6% DNA sequencing gel. The gel was dried and exposed directly to X-ray film.

Reamplification of cDNAs

Double-stranded cDNA bands representing mRNAs differentially expressed between SKOV-3 and SKOV-$3_{TR}$ were excised from the dried gels and reamplified by 40 cycles of PCR using the corresponding set of the primers. Amplified cDNA fragments were purified, labelled with $^{32}$P by the MEGAPRIME DNA labeling system (Amersham, Little Chalfont Buckinghamshire, England), and then used as probes for Northern blot analysis.

Cloning and Sequencing of cDNAs

Reamplified cDNA fragments were cloned into the PCRII vector using the TA CLONING® System (Invitrogen, Carlsbad, Calif.) according to the manufacturer's instructions. Plasmids were prepared using WIZARD® Plus Minipreps DNA Purification System (Promega, Madison, Wis.). cDNAs were sequenced using the AMPLICYCLE Sequence Kit (Perkin Elmer, Branchburg, N.J.) and the DNA SEQUENCER (Model 377A, Applied Biosystems).

Nucleic acid homology searches were performed using the Blast program at the National Center for Biotechnology Information (National Institutes of Health, Bethesda, Md.).

Isolation of TRAG-3 cDNA Clones

After initial PCR screening of the QUICK-SCREEN™ Human cDNA Library Panel (Clontech, Palo Alto, Calif.), a human kidney cDNA library (Clontech) was chosen and screened by PCR and filter hybridization. The kidney cDNA library was initially plated using a higher density than done for filter hybridization, as TRAG-3 is expressed at very low levels in this library. The phase from each plate were soaked in lambda dilution buffer to generate starting aliquots for PCR. Positive aliquots from the primary plating were identified and replated at lower densities to generate sub-aliquots for secondary and tertiary screenings. After three rounds of dilution and PCR selection, the selected diluted library was plated and a single positive clone was confirmed by filter hybridization. Sequence of the plaque purified phase confirmed TRAG-3 isolation.

RNA Isolation and Northern Analyis

RNA was isolated as described above, fractionated by electrophoresis in 1.2% agarose formaldehyde gel (approximately 5 μg total RNA per lane), and transferred to HYBOND N-PLUS membrane (Amersham). RNA was cross-linked to the membrane by a UV crosslinker. $^{32}$P-labelled cDNA probes were used for hybridization as described above. The hybridized membrane was washed twice at room temperature with 2×SSC, 0.1% SDS for 15 minutes, and then twice at 65° C. with 0.2×SSC, 0.1% SDS for 15 minutes. The membrane was exposed to REFLECTION™ Autoradiography X-ray film with an intensifying screen. To confirm the amounts of RNA loaded in each lane, the membrane was later hybridized with a β-actin probe.

Genomic Analysis of TRAG-3

Southern blot analysis of TRAG-3 in a human placenta control, ovarian tumor cell lines SKOV-3 and SKOV-$3_{TR}$, and melanoma cell line K-1 revealed a sequence in each lane corresponding to TRAG-3 and indicating no gene rearrangement. Ethidium bromide staining of the agarose gel showed equal loading of DNA samples. This data suggested that the gene is not genomically amplified but, rather controlled at a transcriptional level.

DNA Isolation and Southern Analysis cell line DNA was extracted using the QIAamp Blood Kit (Qiagen, Valencia, Calif.). Approximately 20 g of genomic DNA, including a human placenta DNA control (SIGMA), was digested with EcoRI (Promega) for 24 h at 37° C.

DNA was then separated by electrophoresis in a 0.9% agarose gel, transferred to a Hybond-N plus membrane (Amersham) using the capillary transfer method with a high salt buffer, and uv-crosslinked. TRAG-3 cDNA probe was 32P labeled using Megaprime DNA labeling system (Amersham) and hybridized to blot. The membrane was washed, exposed, and developed as described above for Northern analysis.

RT-PCR Analysis of TRAG-3

RNA was reverse transcribed using Maloney murine leukemia virus reverse transcriptase (Promega, Madison, Wis.) and an oligo dT primer (Gibco). The primers used for amplification of TRAG-3 were designed according to the published TRAG-3 sequence (GenBank accession number, AF080246). PCR was performed by GeneAmp PCR System 9600 (Perkin Elmer). After the reaction mixtures were incubated at 94° C. for 12 min, 30 cycles began at 94° C. for 30s, 55° C. for 30s, and for 40s, also an 8 min extension step was included at 72° C. PCR products were analyzed by 1.2% agarose gel electrophoresis and results were photographed.

Immunohistochemistry

Melanoma cell lines Meljuso and K-4 were cultured in slide chambers for 24 h. Cells were fixed with acetone and incubated for 20 min with blocking serum. Slides were then incubated with TRAG-3 antibodies for 30 min. After washing with PBS (Bio Whittaker, Walkersville, Md.) slides were incubated with an anti rabbit antibody for 30 min. Staining was performed using Vectastain ABC kit according to the manufacturer's protocol.

TRAG-3 Gene Transfection pCI-neo Mammalian Expression Vector (Promega) was used to overexpress TRAG-3 cDNA in SKOV-3 cells. Constructs carrying TRAG-3 were introduced into SKOV-3 cells by using the PERFECT™ Transfection Kit (Invitrogen) according to the manufacturer's protocol. The individual G418 (300 μg/ml) resistant clones were isolated and examined by Northern analysis for stable expression of TRAG-3. MTT assays were performed on the transfectants to evaluate the effect of TRAG-3 on taxol sensitivity.

Taxol-Resistant SKOV-3 Cell Line

Figure 1:
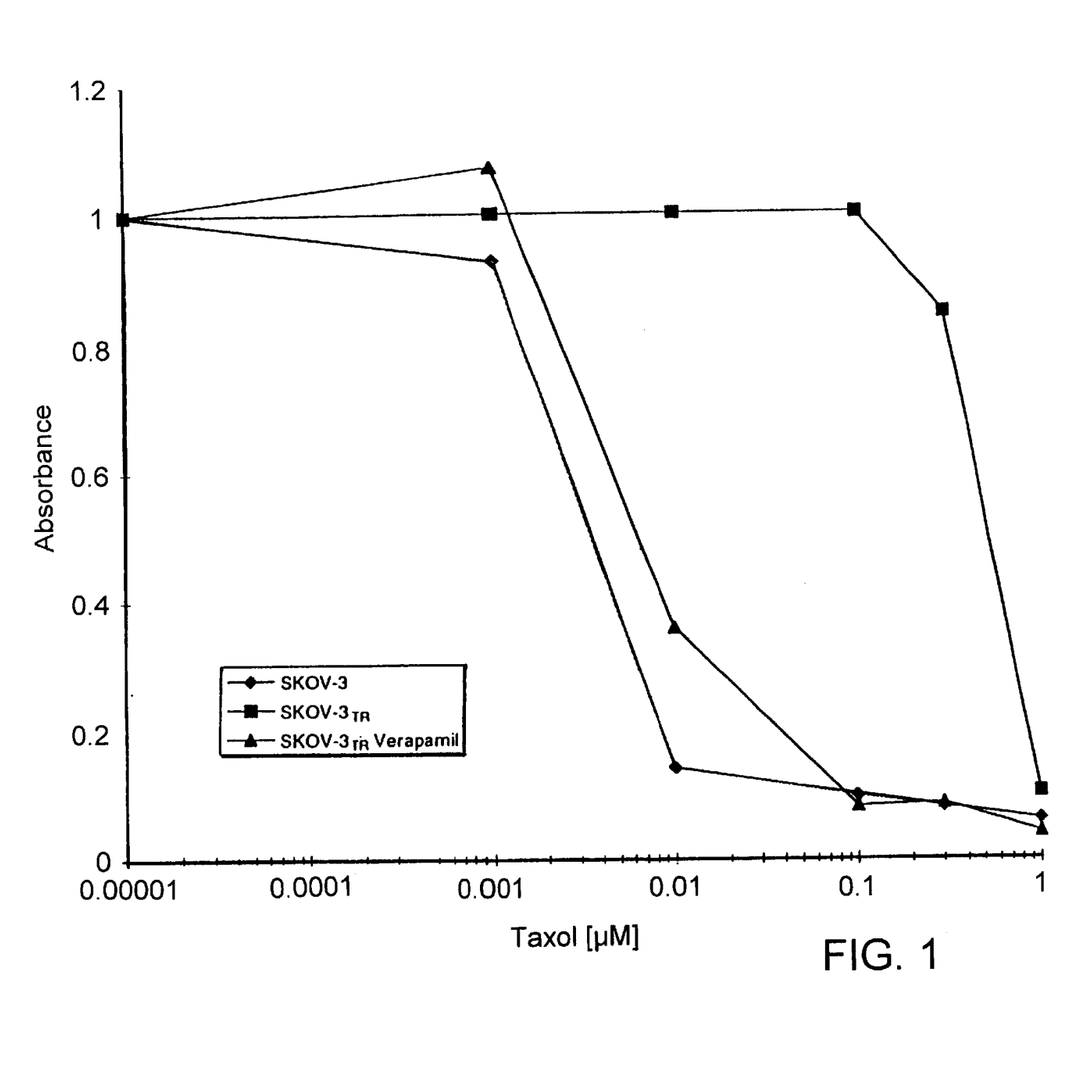
FIG. 1 is a graph showing results of a 3-(4, 5-dimethylthiazol-2-yl)-2,5-diphenyltetrazolium bromide ("MTT") assay that evaluated the effect of taxol and verapamil on SKOV-3 and SKOV-$3_{TR}$ cells.

A taxol-resistant SKOV-3 subline, SKOV-3$_{TR}$, was established by exposing SKOV-3 cells to taxol at stepwise increases in concentration (from 0.00001 μM to 0.3 μM taxol). The resistant phenotype was found to be stable after 18 months of continuous culture in 0.3 μM taxol. The growth rate of SKOV-3, was similar to that of parental SKOV-3. Cell lines were analyzed for their degree of taxol resistance by MTT cytotoxicity assays. SKOV-3$_{TR}$ was found to be approximately 100 fold more resistant to taxol than SKOV-3. SKOV-3$_{TR}$ also demonstrated cross-resistance to vincristine, and to a lesser extent, resistance to doxorubicin. This drug resistance profile is consistent with a MDR1 phenotype. SKOV-3$_{TR}$'s resistance to taxol was reversed in the presence of verapamil, suggesting a MDR1 or MDR1-like mechanism of drug resistance (FIG. 1).

Expression of MDR1 and MRP Genes in SKOV-3$_{TR}$

The SKOV-3 and SKOV-3, cells were evaluated for MDRI and MRP expression by Northern analysis. As compared to parental SKOV-3, SKOV-3$_{TR}$ had an increased MDR1 RNA level, but did not appear to overexpress MRP. Aβ-actin cDNA was used as a probe to normalize the amount of RNA in each lane.

Comparing SKOV-3 and SKOV-3$_{TR}$ by Differential Display

Total RNAs from SKOV-3 and SKOV-3$_{TR}$ were analyzed with 48 primer combinations made from three oligo(dT) primers: H-T$_{11}$M and 16 arbitrary upstream primers. Each primer pair yielded about 100 to 180 bands in each lane, with sizes ranging from 100 basepairs ("bp") to 600 bp. To ensure reproducibility, primer pairs that demonstrated differentially expressed bands were used in a second round of reverse transcription ("RT") and PCR. Complete analysis with the 48 primer sets generated a total of approximately 7200 cDNA fragments for comparison between SKOV-3 and SKOV3$_{TR}$. Among these fragments, 94 were found to be differentially expressed between the two cell lines. 83 of these 94 fragments were successfully reamplified by PCR with the same primer sets and subsequently used as probes (i.e., gene tags) for Northern blot hybridization.

Northern Analysis of Differentially Expressed mRNAs

The aforementioned 83 different gene tags were screened by Northern analysis. The majority of the gene tags either failed to reveal significant differences between SKOV-3 and SKOV-3$_{TR}$ in expression of their target sequences, or did not identify a transcript after a 72 hour exposure. The target transcripts of five of the probes were differentially expressed between SKOV-3 and SKOV-3$_{TR}$. The gene giving rise to one of these five target transcripts was designated TRAG-3. The TRAG-3 transcript was 800 bp long and expressed in SKOV-3$_{TR}$, but not SKOV-3.

To determine whether TRAG-3 is overexpressed in other taxol-resistant cells, applicants used the methods described above to establish five additional taxol-resistant ovarian cell lines CAOV-3 and SW626, and breast cancer cell lines MDA435 and MCF7. Northern analysis demonstrated that TRAG-3 is also overexpressed in the MDA 435 taxol-resistant breast cancer cell line ("MDA 435$_{TR}$") as well as in doxorubicin-resistant cell lines 8226/DOX$_{40}$ and 8226/MDR$_{10}$V. TRAG-3 is not overexpressed in β-tubulin mutant ovarian carcinoma cell lines PTX 10 and PTX 22.

Another differentially expressed gene tag, designated TRAG-1, was found to be overexpressed in both the taxol-resistant SW480 and SKOV-3 cell lines, and in tumors from women with recurrent tumors after taxol treatment. Expression of TRAG-1 was seen in normal tissues including kidney, adrenal, colon, and brain. DNA sequencing and analysis of the TRAG-1 gene tag showed that this gene is novel with no homology to previously reported cDNAs.

Isolation of Full Length TRAG-3 cDNA

Using the 254 bp TRAG-3 gene tag, a human kidney cDNA library was screened and a 620 bp cDNA clone was identified. Homology search in the GenBank/EMBL database showed that TRAG-3 was a previously unappreciated gene contained in a cosmid clone. The sequence of this cosmid provided additional 5' sequence information for TRAG-3. Subsequent RT-PCR confirmed the existence of a 799 bp mRNA transcript.

Figure 2:
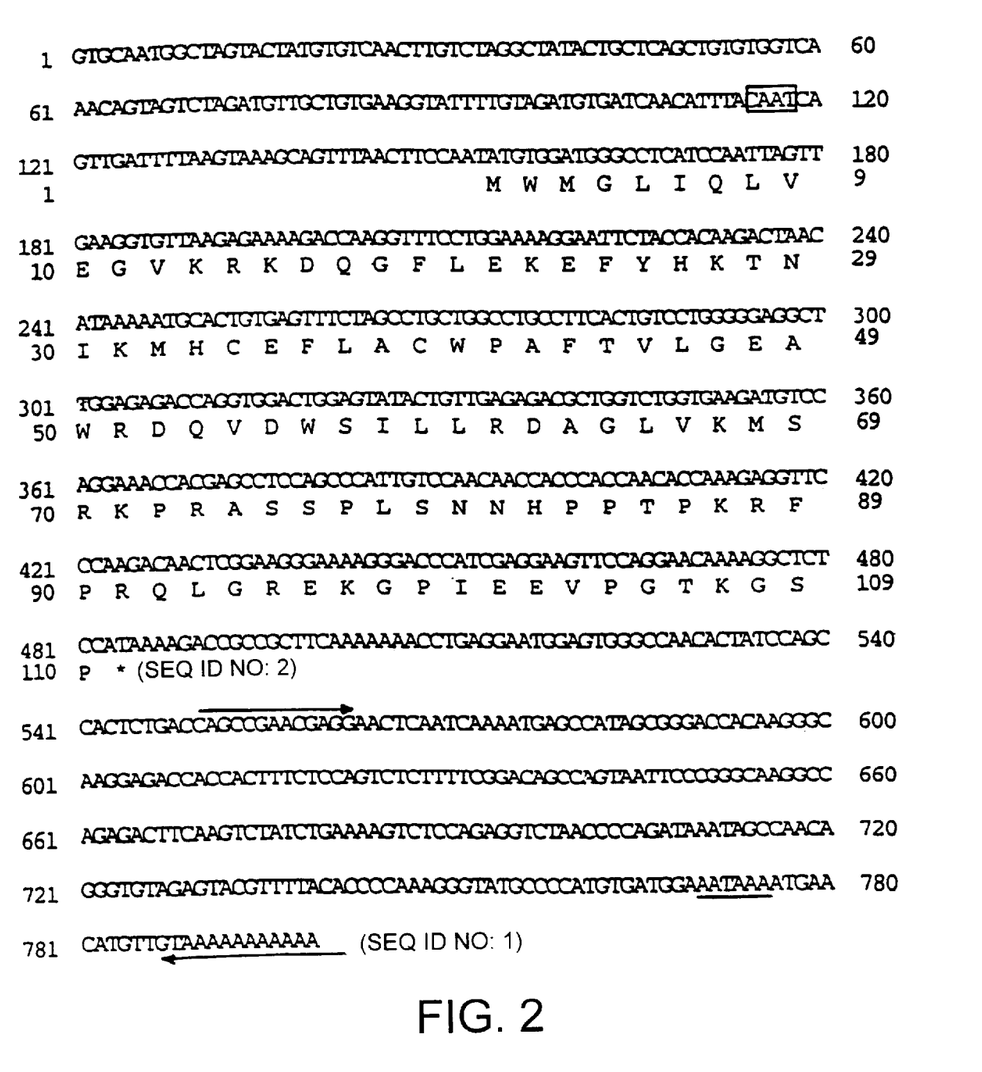
FIG. 2 is the nucleotide sequence (SEQ ID NO:1) of a full-length TRAG-3α cDNA, and deduced amino acid sequence (SEQ ID NO:2) of the TRAG-3α polypeptide encoded by the cDNA. Arrows indicate the annealing sites of the arbitrary and anchored primers, respectively. The portion between these two sites was obtained by initial differential display. The TAA stop codon is denoted by an asterisk. The boxed sequence indicates the position of a potential CAAT sequence motif in the predicted 5' promoter region.

Analysis of this transcript predicts a single open reading frame of 333 bp encoding a polypeptide of 110 amino acid residues. The predicted amino acid sequence contains a hydrophobic amino terminal sequence and a proline-rich carboxy terminal. To applicants' best knowledge, the TRAG-3 polypeptide bears no significant similarities to any known proteins. Sequencing of TRAG-3 from the human kidney cDNA library and cell lines SKOV-$3_{TR}$ and K-562 (ATCC # CCL-243) showed no differences within the coding sequence. Review of the cosmid sequence revealed that the gene is split by a single 125 bp intron. 5' promoter analysis demonstrates a CAAT box 35 bp upstream of the predicted ATG start site (FIG. 2). Other sequences within the cosmid clone tentatively maps this gene to Xq28.

Cell Distribution of TRAG-3

Figure 5:
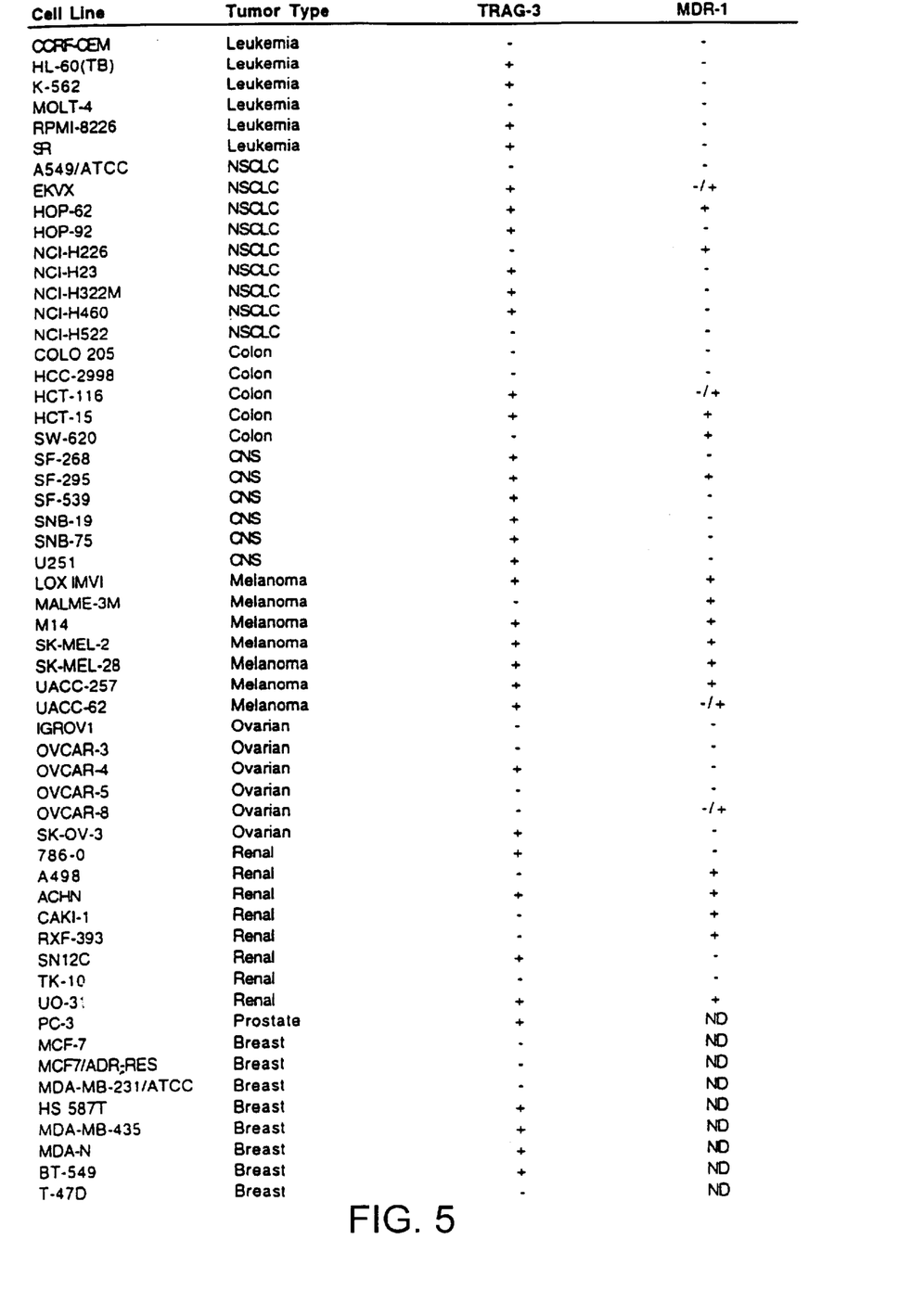
FIG. 5 is a table listing TRAG-3 expression and MDR-1 expression in NCI 60 Cell Line Panel.

Northern blot analyses were performed to determine the distribution of TRAG-3 in normal tissue and tumor cells. Screening of 60 cell lines (FIG. 5), including 56 of the NCI 60 cell line panel, demonstrated TRAG-3 expression in 24 (40%) lines. RT-PCR identifies additional lines with TRAG-3 detection in 33 of 54 (61%).

In contrast, TRAG-3 expression was found absent or at very low levels in normal tissue. Consistent with this founding, RT-PCR of 8 human cDNA libraries demonstrated only weak TRAG-3 expression in kidney and no detectable expression in the libraries of brain, placenta, skeletal muscle, heart, lung, liver and pancreas.

Cell Lines Expressing TRAG-3 Splicing Variants

RT-PCR analysis of TRAG-3 in melanoma cell lines and other tumor cell lines revealed two TRAG-3 transcript sizes, a 799 bp band 850 bp transcript. Sequencing of these transcripts confirmed these results. The two TRAG-3 splice varients, TRAG-3α and TRAG-3β, are predicted to be 110 and 127 amino acid proteins, respectively.

TRAG-3 Expression in Melanoma Cell Lines and Malignant Melanoma Tumor

As reported above, TRAG-3 revealed minimal to absent expression in normal tissues and was overexpressed in 29 of 49 (59%) non melanoma cell lines from the NCI 60 Cell Line Panel. Evaluation of whole RNA by Northern hybridization from 32 melanoma cell lines identified expression of TRAG-3 in 25 of the lines (78%) (FIG. 4). Northern analysis also demonstrated TRAG-3 expression in four of four malignant melanoma tumors.

TRAG-3 Protein Expression in Melanoma Cell Lines

Immunohistochemistry results showed TRAG-3 protein expression in melanoma cell lines. This result was consistent with Northern analysis data.

TRAG-3 Expression in SKOV-3 Transfectants

To elucidate the contribution of TRAG-3 gene product(s) to taxol resistance, taxol-sensitive SKOV-3 cells were lipo-transfected with the pCI/TRAG-3 expression vector. After G418 selection, several TRAG-3 stable transfectant subclones were obtained. These subclones were then examined for taxol sensitivity by MTT assay. Initial results indicated SKOV-3 $T_{TRAG-3}$ transfectants have no significant increase in taxol resistance as compared the parent line.

Transcription Regulatory Activity of TRAG-3

Total RNA was isolated from a TRAG-3 stable transfectant clone and examined for expression levels of several genes by Northern blot analysis. The data showed that zinc finger protein, annexin I, interleukin 6 ("IL-6"), IL-8, macrophage inflammatory protein 2α were overexpressed in the TRAG-3 transfectants, as compared to parental taxol-sensitive SKOV-3 cells. However, the expression of natural killer cell enhancing factor B ("NKEFB") was down regulated in the transfectant as in SKOV-$3_{TR}$, compared to parental cells, which exhibit abundant expression of NKEFB. These results suggest that TRAG-3 act as a transcription factor.

Other Embodiments

The foregoing description is intended to illustrate and not to limit the scope of the invention, which is defined by the scope of the appended claims. Other aspects, advantages, and modifications are within the scope of the following claims.

We claim:

1. An isolated nucleic acid comprising a nucleotide sequence encoding a polypeptide containing an amino acid sequence that is at least 80% identical to SEQ ID NO:2 or 4, wherein expression of the polypeptide in a cell results in an increase in expression of a gene selected from the group consisting of annexin I, interleukin-6, interleukin-8, and macrophage inflammatory protein 2α in the cell; or a decrease in expression of a natural killer cell enhancing factor B gene in the cell.

2. The nucleic acid of claim 1, wherein the amino acid sequence is at least 90% identical to SEQ ID NO:2 or 4.

3. The nucleic acid of claim 2, wherein the amino acid sequence is at least 95% identical to SEQ ID NO:2 or 4.

4. The nucleic acid of claim 3, wherein the amino acid sequence is SEQ ID NO:2 or 4.

5. A vector comprising the isolated nucleic acid of claim 1.

6. A vector comprising the isolated nucleic acid of claim 2.

7. A vector comprising the isolated nucleic acid of claim 3.

8. A vector comprising the isolated nucleic acid of claim 4.

9. A cultured host cell comprising the isolated nucleic acid of claim 1.

10. A cultured host cell comprising the isolated nucleic acid of claim 2.

11. A cultured host cell comprising the isolated nucleic acid of claim 3.

12. A cultured host cell comprising the isolated nucleic acid of claim 4.

13. An isolated nucleic acid comprising a nucleotide sequence that hybridizes to a nucleic acid consisting of the complement of SEQ ID NO:1 or 3 and encodes a polypeptide, wherein the hybridization is conducted under the following conditions: 42° C. in 50% formamide, a first wash in 65° C. in 2×SSC and 1% SDS, and a second wash at 65° C. in 0.1×SSC; and wherein expression of the polypeptide in a cell results in an increase in expression of a gene selected from the group consisting of annexin I, interleukin-6, interleukin-8, and macrophage inflammatory protein 2α in the cell; or a decrease in expression of a natural killer cell enhancing factor B gene in the cell.

14. A vector comprising the nucleic acid of claim 13.

15. A cultured host cell comprising the nucleic acid of claim 13.

* * * * *